United States Patent
Askin, III et al.

(10) Patent No.: US 9,061,134 B2
(45) Date of Patent: Jun. 23, 2015

(54) SYSTEMS AND METHODS FOR FLEXIBLE ELECTRODES

(75) Inventors: Robert E. Askin, III, Salt Lake City, UT (US); Scott D. Hiatt, Salt Lake City, UT (US); Kenneth S. Guillory, Salt Lake City, UT (US); Daniel McDonnall, Salt Lake City, UT (US); Christopher F. Smith, North Salt Lake, UT (US)

(73) Assignee: Ripple LLC, Salt Lake City, UT (US)

( * ) Notice: Subject to any disclaimer, the term of this patent is extended or adjusted under 35 U.S.C. 154(b) by 541 days.

(21) Appl. No.: 12/889,310

(22) Filed: Sep. 23, 2010

(65) Prior Publication Data

US 2011/0237921 A1 Sep. 29, 2011

Related U.S. Application Data

(60) Provisional application No. 61/245,276, filed on Sep. 23, 2009.

(51) Int. Cl.
| | | |
|---|---|---|
| *A61B 5/04* | (2006.01) | |
| *A61N 1/05* | (2006.01) | |
| *A61B 5/0408* | (2006.01) | |
| *A61B 5/0478* | (2006.01) | |
| *A61B 5/0492* | (2006.01) | |
| *A61N 1/375* | (2006.01) | |
| *A61N 1/00* | (2006.01) | |

(52) U.S. Cl.
CPC ........... *A61N 1/05* (2013.01); *A61B 5/0408* (2013.01); *A61B 5/0478* (2013.01); *A61B 5/0492* (2013.01); *A61N 1/375* (2013.01)

(58) Field of Classification Search
CPC . A61N 1/0551; A61N 1/0534; A61N 1/0529; A61N 1/0531; A61N 1/0456; A61N 1/048; A61B 5/0006; A61B 2562/046; H01R 2201/12; H05K 1/118; H05K 1/147; H05K 2201/0133
USPC ......... 600/372–373, 377–378, 382–384, 386, 600/390–393, 544–545; 607/115–118
See application file for complete search history.

(56) References Cited

U.S. PATENT DOCUMENTS

| | | | |
|---|---|---|---|
| 4,566,464 | A | 1/1986 | Piccone et al. |
| 4,735,208 | A | 4/1988 | Wyler et al. |
| 4,850,359 | A | 7/1989 | Putz |
| 4,903,702 | A | 2/1990 | Putz |
| 5,097,835 | A | 3/1992 | Putz |
| 5,279,305 | A | 1/1994 | Zimmerman et al. |
| 5,400,782 | A | 3/1995 | Beaubiah |

(Continued)

*Primary Examiner* — Linda Dvorak
*Assistant Examiner* — Brian M Antiskay
(74) *Attorney, Agent, or Firm* — Phillips Ryther & Winchester; Jared L. Cherry (57) ABSTRACT

Disclosed herein are systems and methods for producing and using electrodes, which may be flexible and/or stretchable, and interconnection structures that can be used both externally and/or implanted within the body. Electrodes according to various embodiments disclosed herein may be produced by depositing patterned layers of insulating and conductive polymers to form multi-layer circuits. The conductive materials and layers in the structure can be exposed on the surface of the structures for use as electrodes. A plurality of electrodes may be formed into an electrode array. In various embodiments, electrode arrays may be associated with telemetry modules configured to wirelessly transmit data collected by the electrode array to a receiver module.

47 Claims, 9 Drawing Sheets

(56) References Cited

U.S. PATENT DOCUMENTS

| | | |
|---|---|---|
| 5,433,742 A | 7/1995 | Willis |
| 5,456,254 A | 10/1995 | Pietroski et al. |
| 5,520,180 A | 5/1996 | Uy et al. |
| 5,681,514 A | 10/1997 | Woody |
| 5,707,367 A | 1/1998 | Nilsson |
| 5,843,155 A | 12/1998 | Axelgaard |
| 5,868,136 A | 2/1999 | Fox et al. |
| 5,895,369 A | 4/1999 | Flower |
| 5,904,712 A | 5/1999 | Axelgaard |
| 5,924,983 A | 7/1999 | Takaki et al. |
| 6,024,702 A | 2/2000 | Iversen |
| 6,091,979 A | 7/2000 | Madsen |
| 6,095,148 A | 8/2000 | Shastri et al. |
| 6,251,978 B1 | 6/2001 | McCullough |
| 6,259,937 B1 | 7/2001 | Schulman et al. |
| 6,304,784 B1 | 10/2001 | Allee et al. |
| 6,480,743 B1 | 11/2002 | Kirkpatrick et al. |
| 6,529,774 B1 | 3/2003 | Greene |
| 6,624,510 B1 | 9/2003 | Chan et al. |
| 6,643,552 B2 | 11/2003 | Edell et al. |
| 6,696,575 B2 | 2/2004 | Schmidt et al. |
| 6,792,314 B2 | 9/2004 | Byers et al. |
| 6,829,498 B2 * | 12/2004 | Rousche et al. ............... 600/378 |
| 6,862,479 B1 | 3/2005 | Whitehurst et al. |
| 6,907,299 B2 | 6/2005 | Han |
| 6,973,342 B1 | 12/2005 | Swanson |
| 6,993,392 B2 * | 1/2006 | Nicolelis et al. ................. 607/45 |
| 7,006,859 B1 * | 2/2006 | Osorio et al. ................. 600/378 |
| 7,027,874 B1 | 4/2006 | Sawan et al. |
| 7,107,097 B2 | 9/2006 | Stern et al. |
| 7,162,308 B2 | 1/2007 | O'Brien et al. |
| 7,190,989 B1 | 3/2007 | Swanson et al. |
| 7,212,851 B2 * | 5/2007 | Donoghue e ................... 600/544 |
| 7,229,437 B2 | 6/2007 | Johnson et al. |
| 7,231,259 B2 | 6/2007 | Jenney et al. |
| 7,234,225 B2 | 6/2007 | Johnson et al. |
| 7,236,834 B2 | 6/2007 | Christopherson et al. |
| 7,264,876 B2 | 9/2007 | Smalley et al. |
| 7,272,427 B2 | 9/2007 | Ristolainen |
| 7,330,756 B2 | 2/2008 | Marnfeldt |
| 7,337,012 B2 | 2/2008 | Maghribi et al. |
| 7,346,391 B1 | 3/2008 | Osorio et al. |
| 7,347,826 B1 | 3/2008 | Karicherla et al. |
| 2004/0243204 A1 * | 12/2004 | Maghribi et al. ............. 607/115 |
| 2005/0143790 A1 | 6/2005 | Kipke et al. |
| 2005/0182423 A1 | 8/2005 | Schulte et al. |
| 2005/0192644 A1 * | 9/2005 | Boveja et al. ................... 607/45 |
| 2006/0058627 A1 | 3/2006 | Flaherty et al. |
| 2006/0129056 A1 | 6/2006 | Leuthardt et al. |
| 2006/0149319 A1 | 7/2006 | Kuo et al. |
| 2006/0224060 A1 | 10/2006 | Garell et al. |
| 2006/0264729 A1 | 11/2006 | Putz et al. |
| 2007/0123963 A1 * | 5/2007 | Krulevitch ................... 607/115 |
| 2007/0167815 A1 | 7/2007 | Jacobsen et al. |
| 2008/0058875 A1 | 3/2008 | Greenberg et al. |
| 2008/0319292 A1 * | 12/2008 | Say et al. ...................... 600/347 |
| 2009/0149913 A1 * | 6/2009 | Putz et al. ...................... 607/45 |
| 2009/0254134 A1 * | 10/2009 | Nikolov et al. ................... 607/3 |

\* cited by examiner

SYSTEMS AND METHODS FOR FLEXIBLE ELECTRODES

RELATED APPLICATIONS

The present application claims the benefit under 35 U.S.C. §119(e) of U.S. Provisional Patent Application No. 61/245,276, filed Sep. 23, 2009, titled "Thin Film Electrode and Interconnect Technology with Optional Integrated Electronics," which application is incorporated herein by reference in its entirety.

FEDERALLY SPONSORED RESEARCH OR DEVELOPMENT

This invention was made with U.S. Government support under contract no.: R44NS061604 awarded by National Institutes of Health. The U.S. Government has certain rights in this invention.

DETAILED DESCRIPTION OF PREFERRED EMBODIMENTS

Disclosed herein are systems and methods for producing and using electrodes, which may be flexible and/or stretchable, and interconnection structures that can be used both externally and/or implanted within the body. Electrodes according to various embodiments disclosed herein may be produced by depositing patterned layers of insulating and conductive polymers to form multi-layer circuits. The conductive materials and layers in the structure can be exposed on the surface of the structures for use as electrodes. A plurality of electrodes may be formed into an electrode array. In various embodiments, electrode arrays may be associated with telemetry modules configured to wirelessly exchange data between an implantable component and an external module.

Certain embodiments may be suited for short-term implantation, while other embodiments may be suited for long-term implantation. Still other embodiments may be used for in vitro applications. Some applications of the systems and methods disclosed herein may include recording from and stimulation of neural tissue, stimulation of muscles, sub- and epi-dural monitoring, use in connection with a blink prosthesis, use in treating incontinence via posterior tibial nerve stimulation, use in restoring sexual function via stimulation of the spinal cord, use in recording implanted EMG and neural signals for use in prosthesis control, use in the stimulation of the recurrent laryngeal nerve for treatment of dystonia, use in stimulation of peripheral nerves for nerve block, and use in connection with neuroprosthetic and neural interface applications (e.g., a pacemaker device).

Multiple types of conductive polymers can be used within the same structure depending on factors, such as cost, conductivity, biocompatibility, and manufacturability for different feature sizes. For example, exposed electrode areas can also be formed from a conductive polymer that is different from conductive polymers used within the structures.

According to various embodiments, electrodes on the surface of the structure can also be formed by embedding metal or other electrode materials into the structures, and connecting to them with conductive polymers. These electrodes may also include geometrical and structural features for penetrating into tissues, hooking or providing mechanical fixation, mitigating stress around flexion points, or increasing the surface area of the electrode. In some embodiments, conducting traces can also be brought to the surface of the structure to create contact pads for bonding to other devices, including sensors, actuators, or other devices or assemblies. Bonding can be performed by applying pressure to hold the conductive areas in contact with bond pads on the devices, or by applying conductive adhesives or joining materials. These joints can also be further encapsulated with insulating polymers, such as silicones to seal and/or structurally reinforce them.

In various embodiments, electrodes may include embedded electronics. Such electronics may include, but are not limited to, any combination of silicon integrated circuits ("ICs"), circuit boards with electronic components, hermetic enclosures with contacts and feed-throughs to internal electronics, and the like. These electronics may include amplifiers, filters, analog to digital conversion, digital signal processing, stimulators, control circuits, fail-safe monitoring, data error checking, batteries, and connections for data and power telemetry with external devices.

Flexible electrodes, according to the present disclosure, may be manufactured by any method for controlled dispensing and/or forming of insulating and conductive polymers into patterns, including: spraying polymer layers onto a surface; depositing polymer layers through needles and narrow dispensing nozzles, including those that use gas pressure and positive displacement for flow control; depositing polymer layers through an ink jet dispenser (such as picodot systems); depositing polymer layers by screen printing and printing through masks; using optical, plasma, or chemical methods to selectively activate areas of a substrate to facilitate selective coating of areas with patterns of polymers; using laser ablation, or plasma or chemical etching (including use of photolithography or overlay masks) to selectively remove and form patterns in layers of deposited polymers; and depositing polymer layers onto both 2D surfaces and 3D molds.

Applications for electrodes, as disclosed herein, may include any application for which electrodes are currently utilized. Certain embodiments may be employed for sensing of electrophysiological signals from cells, tissues, organs, and body parts, including signals from nerves and muscles, EEG, EMG, ECG, EOG, ERG, ENG, ECoG, EGG, LFP, single and multiunit action potentials, and evoked potentials. Sensing and recording can be performed at the cell, tissue, organ, and body part scales, and used for diagnostic purposes, construction of neuroprosthetic systems for functional restoration, and brain machine interfaces to control external devices based on neural and/or muscle signals. These devices can be used for implanted and external body surface applications, as well as for temporary insertion into and/or application to tissues and organs during surgery and diagnostic procedures, for both short- and long-term sensing purposes.

In addition, various embodiments disclosed herein may be utilized for electrical stimulation of cells, tissues, organs, and body parts, including stimulation of nerves and muscles, for diagnostic purposes, enhancing trophic effects, functional restoration or rehabilitation in Functional Electrical Stimulation (FES) and other neuroprosthesis systems, and neuromodulation applications including Deep Brain Stimulation (DBS) targets, the cerebral cortex, sympathetic and parasympathetic nerves, peripheral nerves, and the spinal cord. These devices can be used for implanted and external body surface applications, as well as for temporary insertion into and/or application to tissues and organs during surgery and diagnostic procedures, for both short- and long-term stimulation purposes.

Still other embodiments may be utilized for sensing potentials and currents related to chemical reactions associated with the electrodes, including reactions for oxygen sensing, pH sensing, protein-specific binding of materials to the electrodes, and other chemical sensors based on electrodes. These may also include chemical modification and/or coating of the electrodes, or use of the electrodes with other application-specific materials necessary to sense these reactions.

Flexible electrodes, as disclosed herein, may be also utilized for control or forcing chemical reactions associated with the electrodes, including release of chemicals or drugs, modification of the local chemical environment, and forcing of chemical reactions. These may also include chemical modification and/or coating of the electrodes, or use of the electrodes with other application-specific materials necessary to create or control these reactions. Various embodiments may also be utilized to control chemical reactions, such as gas evolution or pH changes to effect structural changes in materials, including inflation of balloons and changing the shape, rigidity and forces within the device.

Various embodiments disclosed herein may be utilized to generate and sense electrical currents in the body for device operation, implant integrity, and diagnostic and therapeutic use, including imaging and facilitation of trophic effects and promoting recovery and healing of tissues in the body, including nerves or bone, and restoring function to paralytic and paretic body parts. Measurements of electrode and biological material impedances may be collected, including fixed frequency impedance and multi-frequency impedance spectroscopy methods to characterize electrode interfaces and characteristics of cells, tissues, organs, and body parts of humans and animals, including nerve, muscle and dental tissues. Such measurements may include frequency, phase, and all other measures used to characterize impedances.

Still other uses of flexible electrodes, as disclosed herein, may include measurements of biological material impedances, which may used to compute impedance tomography images at the cell, tissue, organ, and body scale; application of potentials for electrophoresis, microelectrode array dish, and other in vitro applications; application of potentials for electroporation and other electrical modifications of tissues; and creation of voltage gradients to accelerate the delivery or migration of drugs.

Various techniques may be utilized in order to facilitate bonding and/or integration of a flexible electrode into a body. For example, adhesives may be applied to the structures to bond them to the body; coatings, such as hydrogels, PEG structures, or other biomaterials, may be used to modulate the tissue response to the structure, including coatings that release drugs for this purpose; coatings may be applied to the electrode to change the adhesion of body tissues to the structures; drugs may be embedded within the non-conducting or insulating material that are released over time to affect the biocompatibility and local tissue response to the implanted structures; chemical surface modification (e.g., hydrophobic, hydrophilic, or non-stick materials) may be utilized to affect the interaction of the surfaces with materials in the environment or biocompatibility in the body; nanomaterials or coatings (e.g., iridium, conductive polymers, or carbon nanotubes) may be applied to electrodes to affect their biocompatibility and impedance; radio-opaque alignment markings, identification information, and/or serial numbers may be embedded into the structures for visualization under x-ray; shapes such as protuberances, pits, holes, or other features may be used to increase the surface area of the electrodes; barbs or hooking features may be included to fix the device within the body; flat tabs, strings, loops or other features may be used to grip, glue, and/or suture the electrode for fixation within the body; or a fabric mesh (such as Dacron) may be used for suturing and/or forming strong tissue adhesions to portions of the structure;

Flexible electrodes disclosed herein may be implanted into the body with a variety of methods, including: insertion into epidural and subdural spaces through openings in the cranium; folding/unfolding and/or rolling/unrolling to deploy the structure once inside the body; use of saline and/or air balloons within the structure to affect mechanical changes inside the body for fixation, application of pressure, guidance, manipulation of placement, or other purpose; use of guide needles and other surgical instruments to create pilot holes and channels for insertion of the structures into the tissue; and use of needles or other surgical instruments to push or pull the structures into the tissue, then removing the instruments while leaving the structures in place.

According to various embodiments, insulated conductors may be disposed within a flexible electrode. Providing insulated conductors within the flexible electrode may also allow for the connection of embedded electrodes; the connection of probes and sensors (e.g., accelerometers, pressure sensors, optical and IR sensors, contact switches, magnetic field sensors, capacitive sensors, inductive coils, thermal flux sensors, temperature sensors, proximity sensors, piezo sensors, ultrasound transducers, sound sensors, etc.); the connection of actuators or devices (e.g., force generators, motors, piezo actuators, electromagnets, coils, inductors, ultrasound transducers, stimulators, light emitting diodes etc.); the formation of flexible elastic resistor and capacitor elements that can stretch around tissues and detect structural changes in the sensor by changes in electrical impedance in the sensor elements; the formation of capacitive shields and guard traces for protection of other traces within the structure from interference and electrostatic discharge (ESD); and the measurement of conductivity within the electrode and electrode structures to diagnose problems within the device structure.

Figure 1:
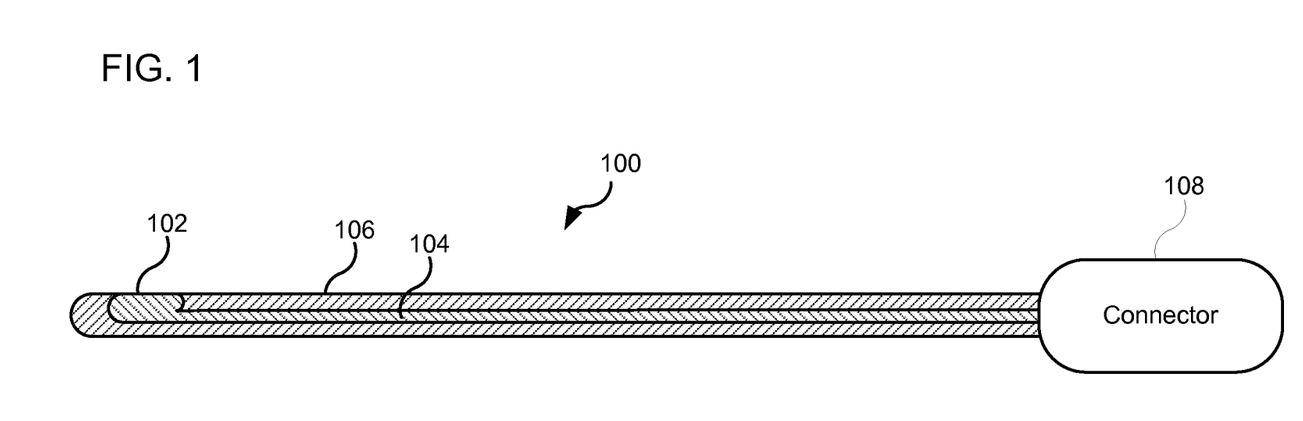
FIG. 1 illustrates a cross-sectional view of one embodiment of an electrode.

FIG. 1 illustrates a cross-sectional view of one embodiment of an electrode 100, according to the present disclosure. Electrode 100 includes an internal conductive polymer trace 104 that is disposed within an insulating polymer 106. An electrode interface 102 may be in electrical communication with internal conductive polymer trace 104. Internal conductive polymer trace 104 may also be in electrical communication with a connector 108. According to various embodiments, connector 108 may comprise a percutaneous or transcutaneous connector.

Insulating polymer 106 may comprise any flexible and/or elastomeric material that provides electrical insulation. According to various embodiments, insulating polymer 106 may comprise any combination of silicones, siloxanes, polydimethylsiloxane (PDMS), rubber materials, latex materials, polyesters, polypropylenes, polytetrafluoroethylenes (PTFE), Parylenes, liquid crystal polymers, polyimides, polyesterimides, polyamides, polybutyldienes (PBD), flexible copolymers, or any other polymer used for medical applications.

Internal conductive polymer trace 104 may comprise polymers that are intrinsically conductive (including polypyrrole, polyacetylene, polyaniline or poly[dioctyl-bithiophene] (PDOT)), or polymers that are doped with conductive particles. Any type of conductive particle may be utilized in connection with internal conductive polymer trace 104, including any combination of: conductive forms of carbon (including graphite, carbon black, vitreous carbon, acetyl carbon, and carbon nantotubes); metal particles (e.g., particles of silver, gold, platinum, iridium, platinum-iridium alloys, titanium, tungsten, stainless steel); particles of other materials (e.g., nickel, ceramics, or carbon) that are coated with metals with higher contact conductivity (e.g., silver, gold, iridium, and platinum). Further, according to various embodiments, particles of shapes and morphologies may be utilized to better facilitate electrical contact between conductive particles in the polymer. According to various embodiments utilizing polymers doped with conductive particles, conductive particles may be pre-mixed into the polymer that is subsequently formed into an electrode, may be simultaneously mixed with a polymer and dispensed to form an electrode, or may be injected into a previously dispensed polymer layer with a carrier material (e.g., toluene or alcohol).

According to various embodiments, the design and manufacturing of the flexible devices may also include: use of polymers that are made conductive by filling with conductive particles, and in which the polymer shrinks to keep conductive particles in compression; polymers that shrink, expand, and/or soften after curing or when exposed to the body, to introduce stresses and/or shape changes into the material and/or other changes in mechanical compliance; substrate layers that are stretched during application of other layers, to keep the secondary layers in compression when the substrate is relaxed; other materials and fibers (including carbon or glass fibers) embedded into the structures to provide mechanical strain reinforcement and/or affect the mechanical properties of the structure in homogeneous and complex heterogeneous arrangements; coatings (such as polyethylene glycol) that stiffen the structure to aid insertion into tissues, that soften or dissolve away over time; formation of twisted-pair cables and/or cable ground planes within the structure; use of magnetic fields to manipulate conductive polymers with particles that respond to magnetic fields; plasma cleaning or other types of surface activation and adhesion promotion methods (such as silanes or other compounds) applied to polymer layers to enhance their bonding and reduce the chances of delamination.

Figure 2:
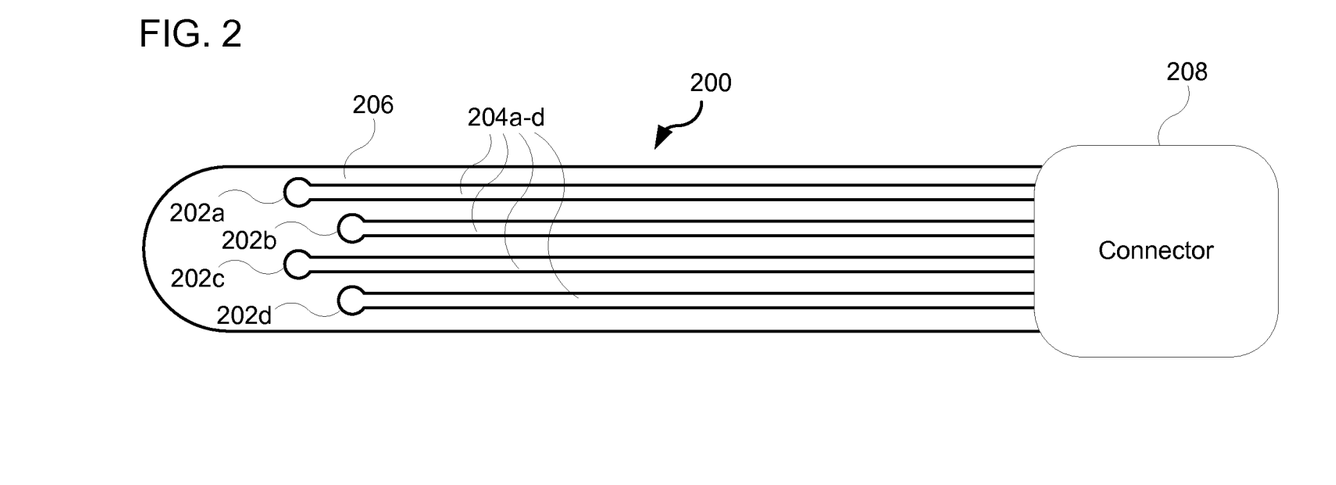
FIG. 2 illustrates a top view of one embodiment of an electrode.

FIG. 2 illustrates a top view of one embodiment of an electrode 200 according to the present disclosure. Electrode 200 includes a plurality of internal conductive polymer traces 204a-d surrounded by an insulating polymer 206. A plurality of electrode interfaces 202a-d power in electrical communication with internal conductive polymer traces 204a-d, respectively. Although FIG. 2 illustrates an embodiment including four electrode interfaces 202a-d associated with four internal conductive polymer traces 204a-d, according to various embodiments, any number of electrode interfaces 202 may be utilized in connection with any number of internal conductive polymer traces 204. Internal conductive polymer traces 204a-d are also in electrical communication with connector 208.

Figure 3A:
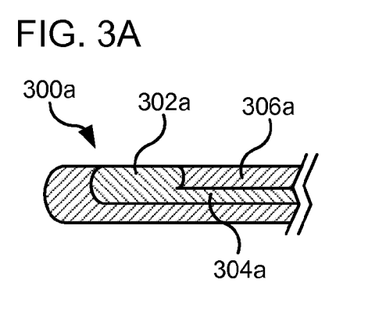
FIGS. 3A, 3B, and 3C are cross sectional views that illustrate three embodiments of electrodes.
Figure 3B:
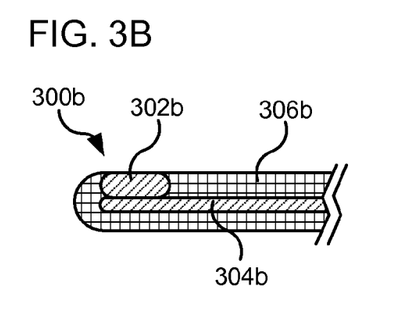
Figure 3C:
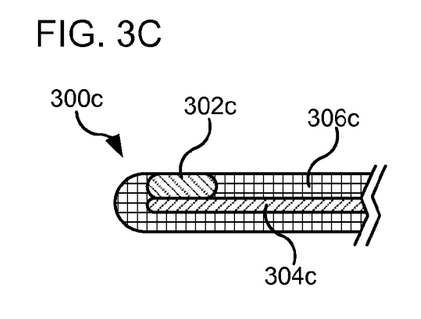

Multiple types of conductive polymers can be used within the same structure, depending on factors such as cost, conductivity, biocompatibility, and manufacturability for different feature sizes. FIGS. 3A-3C are cross sectional views that illustrate three embodiments of electrodes 300a-c, which may be utilized in various embodiments. FIG. 3A illustrates electrode 300a, in which the same material forms both an internal conductive polymer trace 304a and an electrode interface 302a. An insulating polymer 306a is disposed around electrode interface 302a and internal conductive polymer trace 304a. FIG. 3B illustrates electrode 300b, in which an internal conductive polymer trace 304b comprises one polymer, and an electrode interface 302b comprises a second polymer. An insulating polymer 306b is disposed around electrode interface 302b and internal conductive polymer trace 304b. FIG. 3C illustrates electrode 300c, in which an electrode interface 302c is comprised of metal. Electrode interface 302c is in electrical communication with an internal conductive polymer trace 304c. An insulating polymer 306c is disposed around electrode interface 302c and internal conductive polymer trace 304c.

Electrode interfaces 302a-c may, in various embodiments, include geometrical and structural features for penetrating into tissues, hooking or providing mechanical fixation, or increasing the surface area of the electrode. Bonding between electrode interfaces 302b-c and internal conductive polymer traces 304b-c can be performed by the application of pressure to hold the conductive areas in contact, or by applying conductive adhesives or joining materials. These joints can also be further encapsulated with insulating polymers such as silicones to seal and/or structurally reinforce them.

Figure 4A:
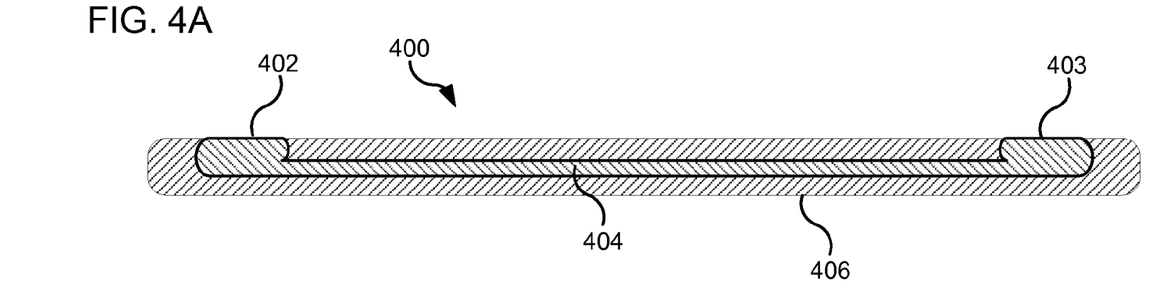
FIG. 4A illustrates a cross sectional view of one embodiment of an electrode comprising two electrode interfaces.

FIG. 4A illustrates a cross sectional view of one embodiment of an electrode 400 comprising two electrode interfaces 402 and 403. Electrode interfaces 402 and 403 are in electrical communication by way of internal conductive polymer trace 404. Electrode interfaces 402 and 403 and internal conductive polymer trace 404 are surrounded by insulating polymer 406. Embodiments including multiple electrode interfaces, such as electrode 400, may allow for the connection of other devices, including sensors, actuators, or other devices or assemblies to electrode 400.

Figure 4B:
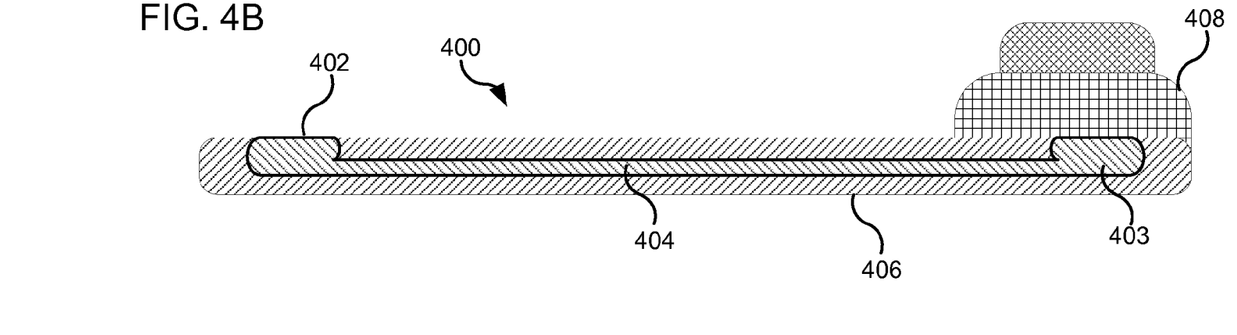
FIG. 4B illustrates a cross sectional view of an electrode that includes a connector in electrical communication with an electrode interface.

FIG. 4B illustrates a cross sectional view of electrode 400 that also includes a connector 408 in electrical communication with electrode interface 403. Various embodiments may also include connectors, including percutaneous connectors that pass out of the body. Such connectors may, in various embodiments, be encased in titanium, sintered titanium, stainless steel, polymer fabrics, or other materials to facilitate better biocompatibility and infection resistance for percutaneous applications. These connectors may also include screw holes, mounting flanges, rings, loops, fasteners, fabrics, or other structures for fixing the connector to tissue, skin, and/or bone.

Figure 5:
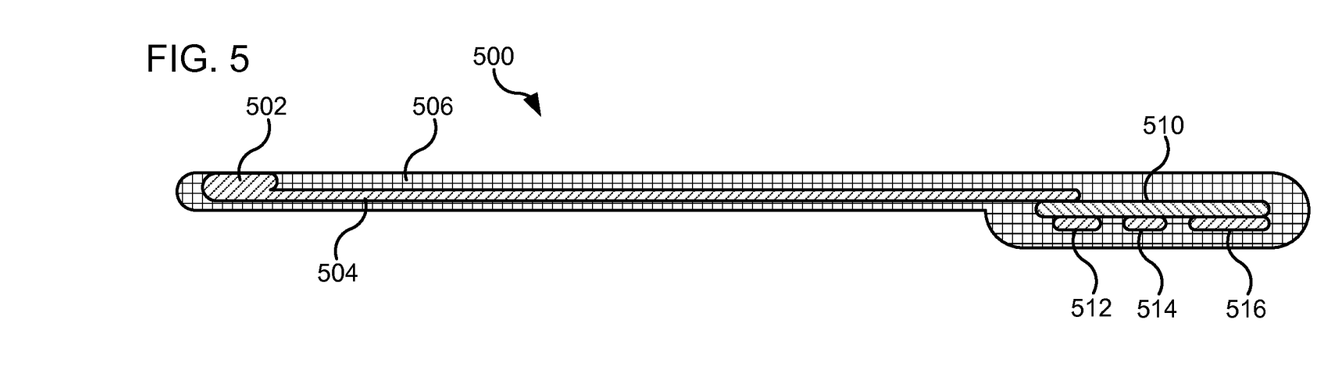
FIG. 5 illustrates a cross sectional view of one embodiment of an electrode that includes an electronic package.

FIG. 5 illustrates a cross sectional view of one embodiment of an electrode 500 that includes a printed circuit board 510 and various electronic components 512, 514, and 516. Electrode 500 also includes an electrode interface 502 in electrical communication with an internal conductive polymer trace 504. An insulating polymer 506 may be disposed around internal conductive polymer trace 504, printed circuit board 510, and various electronic components 512, 514, and 516. According to various embodiments, a variety of electronic components may be integrated with a printed circuit board 510. For example, such electronic components may include amplifiers, stimulators, data transmission circuitry, light emitting diodes and/or photo sensing diodes, data processing circuitry, batteries, and/or circuitry for receiving power from an external power source.

Figure 6:
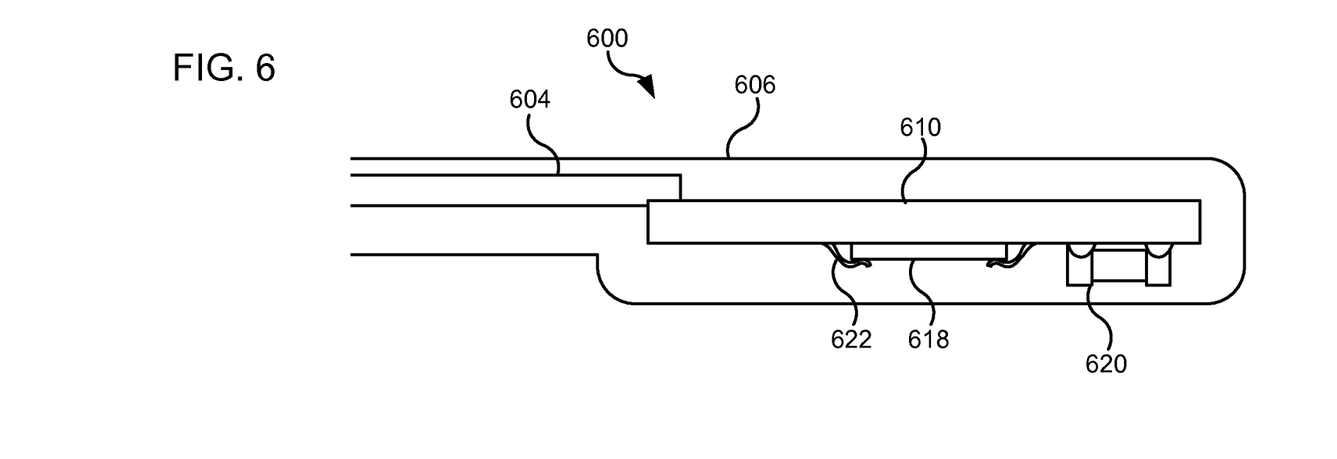
FIG. 6 illustrates a side view of one embodiment of an electrode that includes a printed circuit board, which is coupled to an optical transceiver and an application specific integrated circuit.

FIG. 6 illustrates a side view of an electrode 600 that includes a printed circuit board 610, which is coupled to a transceiver 620, and an application specific integrated circuit 618. An insulating polymer 606 may be disposed around an internal conductive polymer trace 604, printed circuit board 610, application specific integrated circuit 618, and transceiver 620. Wire leads 622 may electrically connect a printed circuit board 610 to application specific integrated circuit 618.

Certain embodiments may utilize infrared data transmission in order to transmit data collected by electrode 600 to an external data receiver (not shown). Such embodiments may comprise materials with optical properties selected for selective transparency to certain optical or infrared signals so that the device can use these wavelengths for telemetry. For example, insulating polymer 606 may be selected so as to provide minimal attenuation to an infrared data signal generated by transceiver 620.

Figure 7:
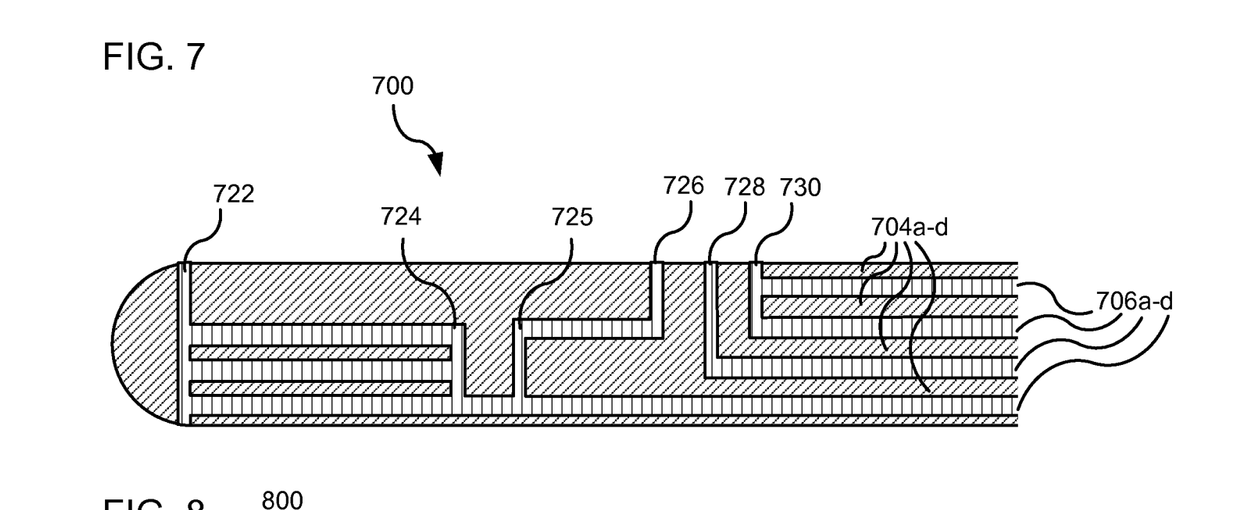
FIG. 7 illustrates a cross sectional view of one embodiment of a multi-layer electrode.

FIG. 7 illustrates a cross sectional view of one embodiment of a multi-layer electrode 700. Electrode 700 comprises a plurality of internal conductive polymer traces 706a-d separated by a plurality of insulating layers 704a-d. Electrode 700 includes conductive vias 722, 724, 726, 728, and 730 that connect between internal conductive polymer traces 706a-d and/or the surface of electrode 700. Electrode 700 includes through via 722, which passes through all conductive layers to the surface of electrode 700; blind vias 726, 728, and 730, which pass from the surface of electrode 700 to some conductive layers; and buried vias 724 and 725, which are completely embedded within electrode 700.

Figure 8:
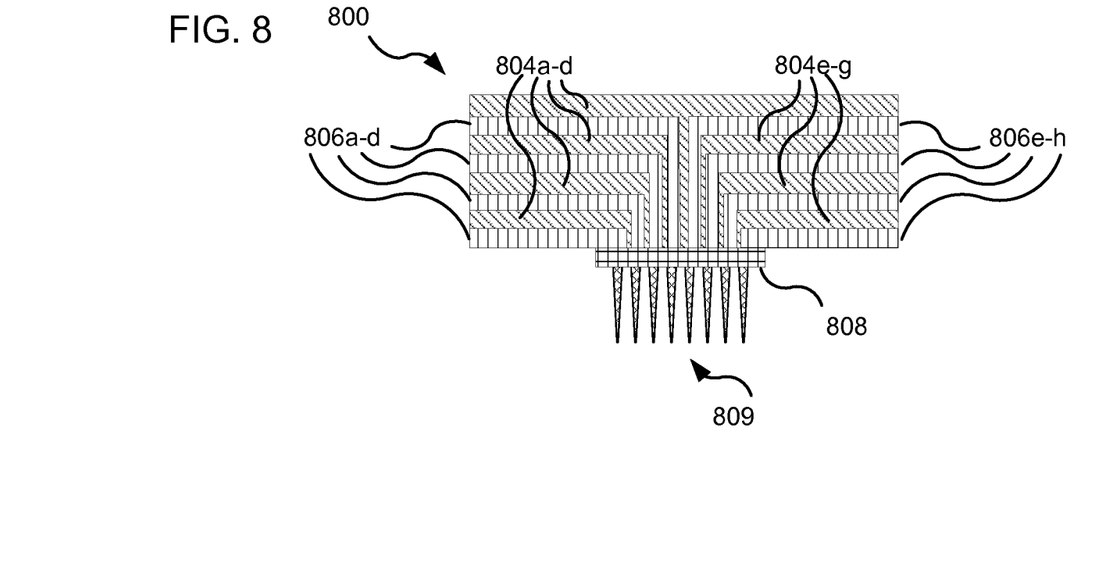
FIG. 8 illustrates a cross-sectional view of one embodiment of a multi-layer electrode and a connector.

FIG. 8 illustrates a cross-sectional view of one embodiment of a multi-layer electrode 800 and a connector 808. Connector 808 may comprise a plurality of penetrating electrodes 809, which although not shown in a grid configuration in FIG. 8, may be arranged in a grid configuration. A plurality of internal conductive polymer traces 806a-h may be in electrical communication with the plurality of penetrating electrodes 809. A plurality of insulating polymer layers 804a-g may be disposed between the plurality of internal conductive polymer traces 806a-h. Accordingly, electrical signals may be confined to internal conductive polymer traces 806, which may in turn be transmitted to an external connector.

Figure 9:
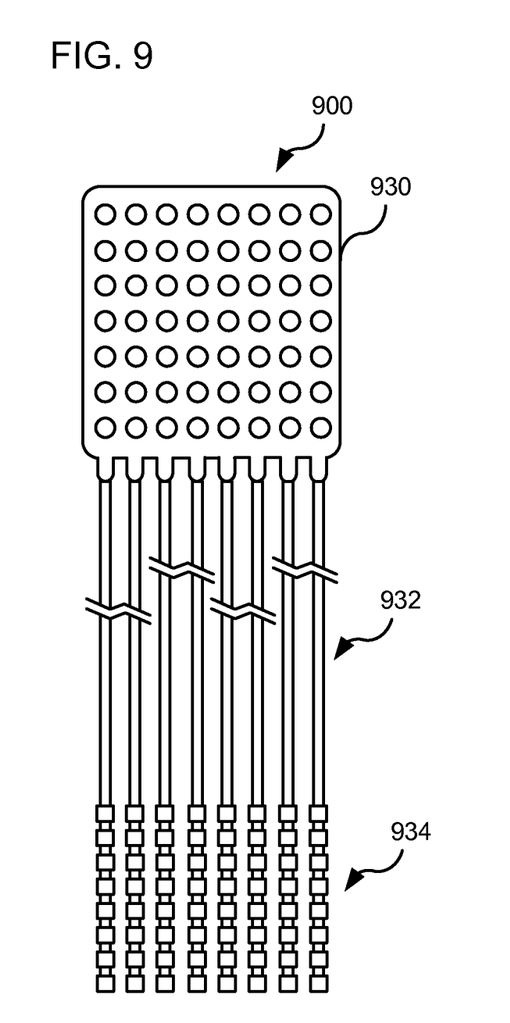
FIG. 9 illustrates one embodiment of an electrode array.

FIG. 9 illustrates one embodiment of an electrode array 900. Electrode array 900 may include an electrode grid 930 that includes a plurality of individual electrodes. Although FIG. 9 illustrates a square electrode array 900, having eight electrodes on each side, any number of configurations may also be utilized in alternative embodiments. Each electrode in electrode grid 930 may be in electrical communication with an internal conductive polymer trace (not shown). A plurality of internal conductive polymer traces may be grouped in one of a plurality of lead wires 932. Lead wires 932 may also be an electrical communication with the plurality of leads 934. Electrical signals received by each of the plurality of electrodes in electrode grid 930 may be conducted to one of the plurality of leads 934.

In one embodiment, electrode array 900 may be utilized for intracranial epilepsy monitoring. Some of the patients suffering from epilepsy that do not respond adequately to drug therapies are candidates for surgical treatment to resect or disrupt seizure foci. In preparation for such a surgery, an electrode array, such as electrode array 900, may be implanted over the focal areas for up to 30 days to accurately localize the seizure foci and minimize damage to surrounding cortical areas. According to various embodiments, electrode arrays may range in size from large grids (e.g., 9 cm×9 cm) to small strips of electrodes (e.g., 1 cm×6 cm). Additional embodiments include high density microECoG electrodes which may be present in conjunction with larger conventional cortical mapping electrodes. After implantation, lead wires 932 may connect the implanted electrode array to a neural instrumentation system (not shown), which records information regarding electrical conditions detected by the plurality of electrodes in electrode grid 930. Lead wires 932 may pass through the scalp of the patient. The use of percutaneous lead wires 932 may expose patients to a risk of infection.

Figure 10A:
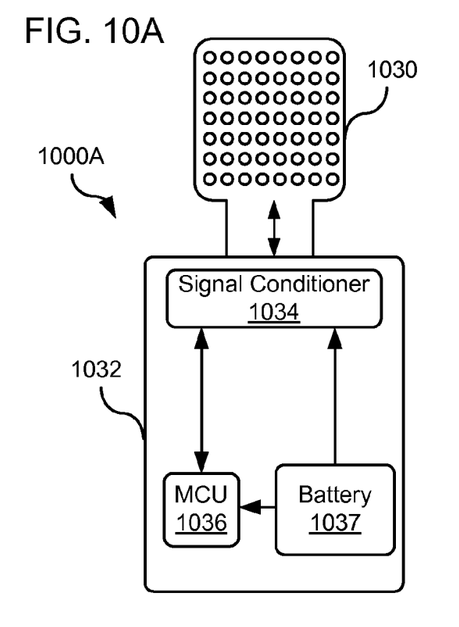
FIG. 10A illustrates a block diagram of one embodiment of an implantable system that includes an electrode grid and a signal processing unit.

FIG. 10A illustrates a block diagram on one embodiment of an implantable system 1000A that includes an electrode grid 1030 and a signal processing unit 1034. According to various embodiments, system 1000A may be utilized in a variety of applications, including deep brain stimulation and intracranial monitoring. Electrode grid 1030 is in electrical communication with signal processing unit 1034 and may exchange data with signal processing unit 1034. Data may be received by signal processing unit 1034 and recorded and/or data may be transmitted from signal processing unit 1032 to electrode grid 1030 in order to provide electrical stimulation. Data sent to or received from electrode grid 1034 may be conditioned by signal conditioner 1034. Such conditioning may include, in various embodiments, amplification, analog to digital conversion (e.g., conversion of analog data recorded by electrode grid 1030 to digital data), and digital to analog conversion (e.g., conversion of digital data from signal processing unit 1032 to analog data). A microprocessor unit ("MCU") 1036 may be in electrical communication with signal conditioner 1034, and may record, analyze, and/or generate data signals received from work to be sent to electrode grid 1030. A battery 1037 may provide power to MCU 1036 and signal conditioner 1034.

Figure 10B:
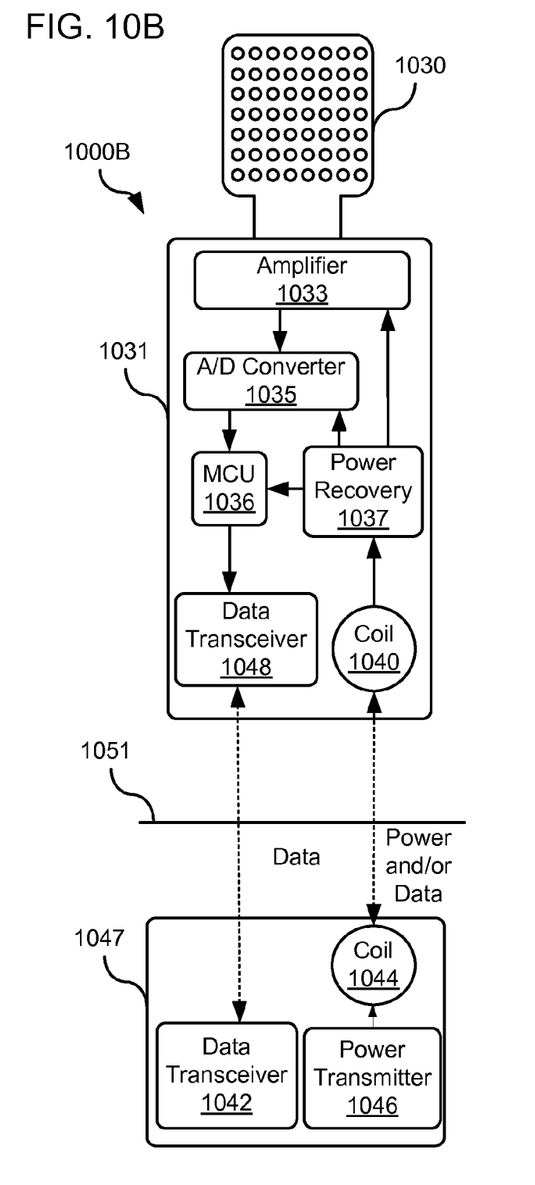
FIG. 10B illustrates a block diagram of one embodiment of a wireless system that includes an electrode grid, a telemetry module, and a receiver module.

FIG. 10B illustrates a block diagram of one embodiment of a wireless system 1000B that includes an electrode grid 1030, a telemetry module 1031, and a receiver module 1047. In various embodiments, system 1000 may be utilized for intracranial epilepsy monitoring. Telemetry module 1031 and receiver module 1047 may be configured to exchange data and power wirelessly across the patient's skin 1051. In contrast to the embodiment illustrated in FIG. 9, system 1000 does not include percutaneous lead wires, and accordingly, use of system 1000 may reduce the risk of infection to a patient associated with percutaneous lead wires.

The electrode grid 1030 is in electrical communication with a telemetry module 1031. Telemetry module 1031 includes an amplifier 1033, which receives and amplifies signals collected by each of the plurality of individual electrodes. Amplifier 1033, in one particular embodiment, may comprise analog amplifier components, such as those available from Intan, Technologies, LLC of Salt Lake City, Utah. Amplified signals generated by amplifier 1033 may be converted to digital signals by A/D converter 1035. According to various embodiments, A/D converter 1035 may also comprise a multiplexer configured to generate a digital output from a plurality of analog inputs.

A microprocessor unit (MCU) 1036 may receive and process the output of A/D converter 1035. According to various embodiments, MCU 1036 may comprise a commercially available microcontroller, or may comprise an application specific integrated circuit. In one particular embodiment, MCU 1036 may be embodied as a microprocessor in the TI MSP430 product family available from Texas Instruments of Dallas, Tex. In various embodiments, MCU 1036 may comprise both one-time programmable memory for core software storage and EEPROM memory for device serialization information and special feature programming.

MCU 1036 may prepare data to be transmitted by a data transceiver 1048. In one embodiment data transceiver 1048 may comprise an infrared transceiver, and infrared data may be transmitted via a Return to Zero (RZ) scheme with adaptive thresholding. If further DC balance is needed, 8B10B or Manchester codes may be utilized. All data may include error-checking codes. In an alternative embodiment, data transceiver 1048 may comprise a radio frequency data transmission system.

System 1000 may also include a receiver module 1047, which may be separated from telemetry module 1031 by the skin 1051 of the patient. Receiver module 1047 may comprise a data transceiver 1042. Receiver module 1047 and telemetry module 1031 may exchange data across the patient's skin using a bidirectional communications channel. Data received from telemetry module 1031 may include recorded data from electrode grid 1030, while data transmitted to telemetry module 1031 may comprise data to provide stimulation using electrode grid 1030.

Receiver module 1042 may further comprise a power transmitter 1046, which is coupled to a coil 1044. Coil 1044 may be inductively coupled to coil 1040. Power transferred to coil 1040 may be provided to a circuit for power recovery 1037, which may in turn provide power to A/D converter 1035 and amplifier 1033. According to various embodiments, inductive coupling between coil 1044 and coil 1040 may also be used to transmit data. Circuitry for power recovery circuit 1037 may comprise a resonant full-wave rectifier (not shown) and filter with a low drop-out linear regulator (not shown). Circuitry for power recovery 1037 may also include the ability to measure the over-voltage of the rectifier and pass the signal to MCU 1036 for sampling. This signal passed from circuitry for power recovery 1037 to MCU 1036 may be transmitted to receiver module 1047, and may allow receiver module 1047 to optimize transmitted power to minimize thermal dissipation in circuitry for power recovery 1037. This signal may also be used by the receiver module 1047 to sense coupling strength and alignment of receiver module 1047 relative to telemetry module 1031.

Figure 11:
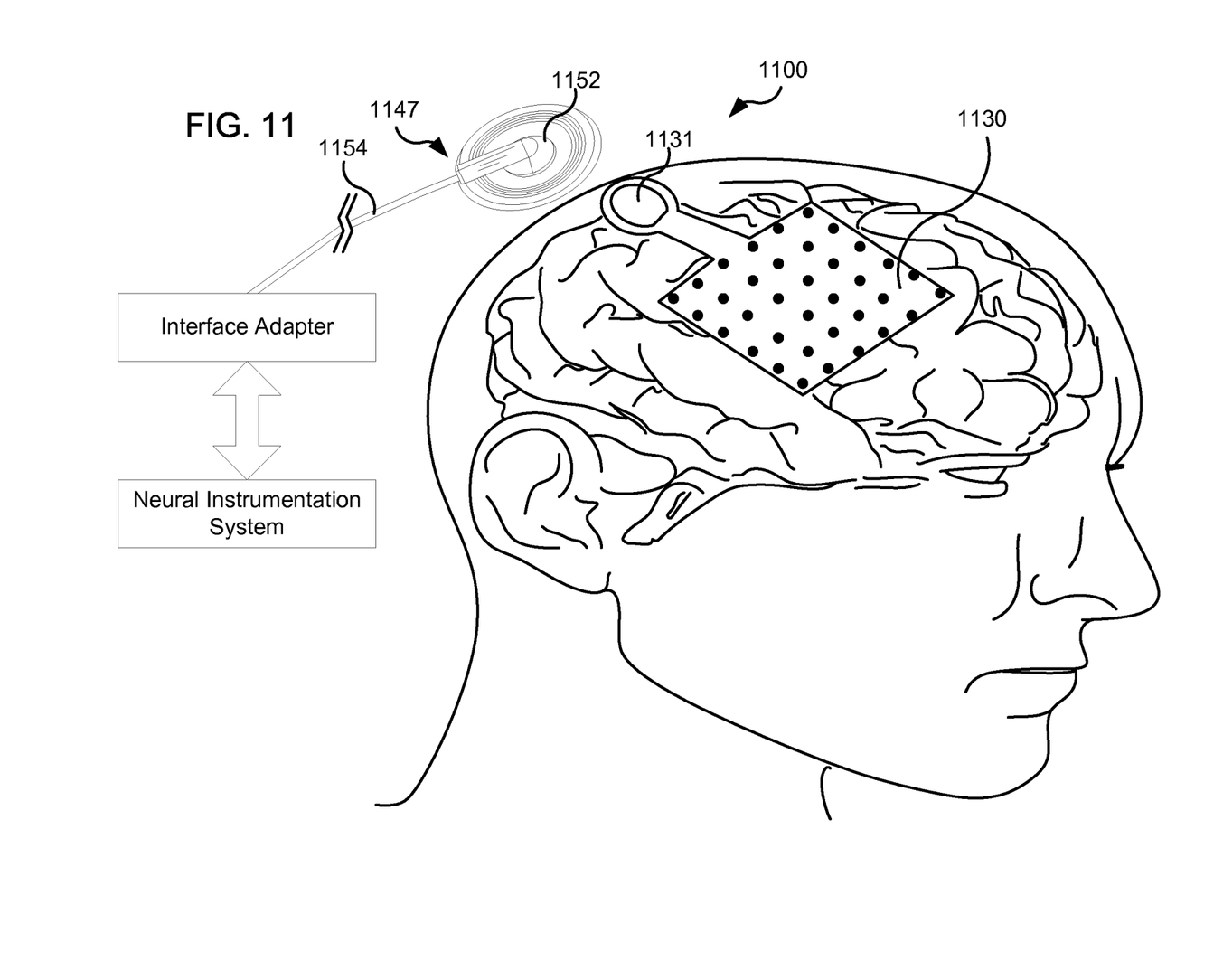
FIG. 11 illustrates one embodiment of a system that comprises an electrode grid, a telemetry module, and a receiver module.

FIG. 11 illustrates one embodiment of a system 1100 that comprises an electrode grid 1130, a telemetry module 1131, and a receiver module 1147. In the illustrated embodiment, electrode grid 1130 and telemetry module 1131 are implanted in a patient. Electrode grid 1130 may be in electrical communication with telemetry module 1131, which may include wireless data and power transmission systems.

Receiver module 1147 may inductively provide power via a coil and may receive a data signal transmitted by telemetry module 1131. The inductive power transfer between receiver module 1147 and telemetry module 1131 may be accomplished using Class E architecture. In various embodiments, system 1100 allows for the adjustment of the carrier used by the inductive power transfer system and for the adjustment of the transmitted power. In one embodiment, an infrared detector (not shown) may be located in the center of receiver module 1147. An infrared-transparent window may be aligned over the infrared detector to provide a light path from an infrared transmitter (not shown) emitter in telemetry module 1131. In various embodiments, a coil for inductive power transfer may be constructed by winding Litz wire around a soft substructure, or the RF coil may be integrated into a flexible receiver printed circuit board. Receiver module 1147 may be fixed to the body by adhesives, compression bands, bandages, or any other methods.

In certain embodiments, an alignment indicator 1152 may be disposed on the receiver module 1147. Alignment indicator 1152 may provide an indication of the relative strength of the telemetry coupling between receiver module 1147 and telemetry module 1131. Alignment indicator 1152 may allow a clinician to find the optimal placement for the receiver module 1147. Certain embodiments may be able to tolerate alignment errors up to 1 cm from center.

Receiver module 1147 may be coupled to a power source and a neural instrumentation system by way of wire 1154. Certain embodiments may feature an interface adapter for connecting the External Transceiver to the Grapevine™ neural instrumentation system, which is available from Ripple, LLC of Salt Lake City, Utah. The Grapevine™ neural instrumentation system is available in both bedside and wearable configurations. The neural instrumentation system may provide for recording of data received by receiver module 1147.

Figure 12:
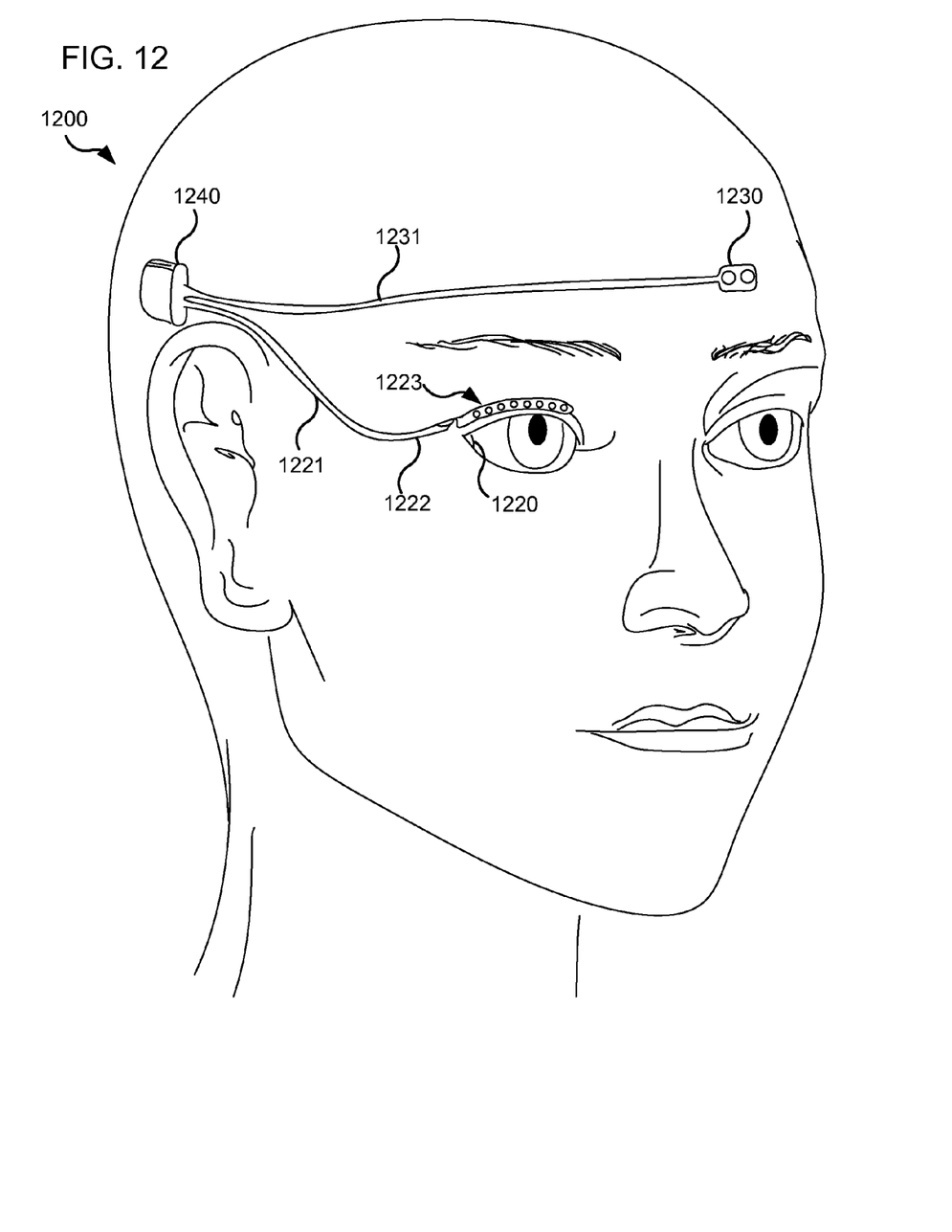
FIG. 12 illustrates one embodiment which includes components for electrical stimulation and/or recording as part of a biocompatible system.

FIG. 12 illustrates an embodiment of a system 1200 that comprises a stimulating electrode array 1220, stimulation leads 1221, a recording electrode array 1230, recording leads 1231, and an electronics module 1240. In the illustrated embodiment, all components are implanted subcutaneously in a patient. The stimulation electrode array 1220 and stimulation leads 1221 may consist of a contiguous structure of layered conductive polymer and insulating substrate materials. Similarly the recording electrode array 1230 and recording leads 1231 may also consist of a contiguous structure of layered conductive polymer and insulating substrate materials. The stimulation 1220 and recording 1230 arrays are electrically connected to the electronics module 1240 via their respective leads 1221 and 1231. The electronics module 1240 communicates with an external module (not shown) in a manner similar to the telemetry protocol outlined between components 1131 and 1147 shown in FIG. 11. The stimulation lead 1221 may also include a mechanical feature 1222 designed to provide additional stress relief around the lateral canthus area to mitigate flexion forces. The stimulation electrode array 1220 may also have a plurality of electrodes 1223 designed to permit the efficient conduction of exogenous charge to paretic and paralytic facial musculature.

This embodiment may be used as a blink prosthesis to restore eyelid function to patients with unilateral facial paralysis. The exogenous electrical charge it injects may functionally activate paretic or paralytic muscles to effect closure of the lid margin. The prosthesis records EMG with an array 1230 implanted in the contralateral neurologically intact hemiface to detect the onset of blink, and uses this detected signal to time stimulation via the implanted electrode array 1220 in the nonfunctioning eyelid to create a synchronous bilateral blink. Stimulation may also provide a trophic effect to permit more complete and more rapid recovery in facial paralysis patients.

Figure 13:
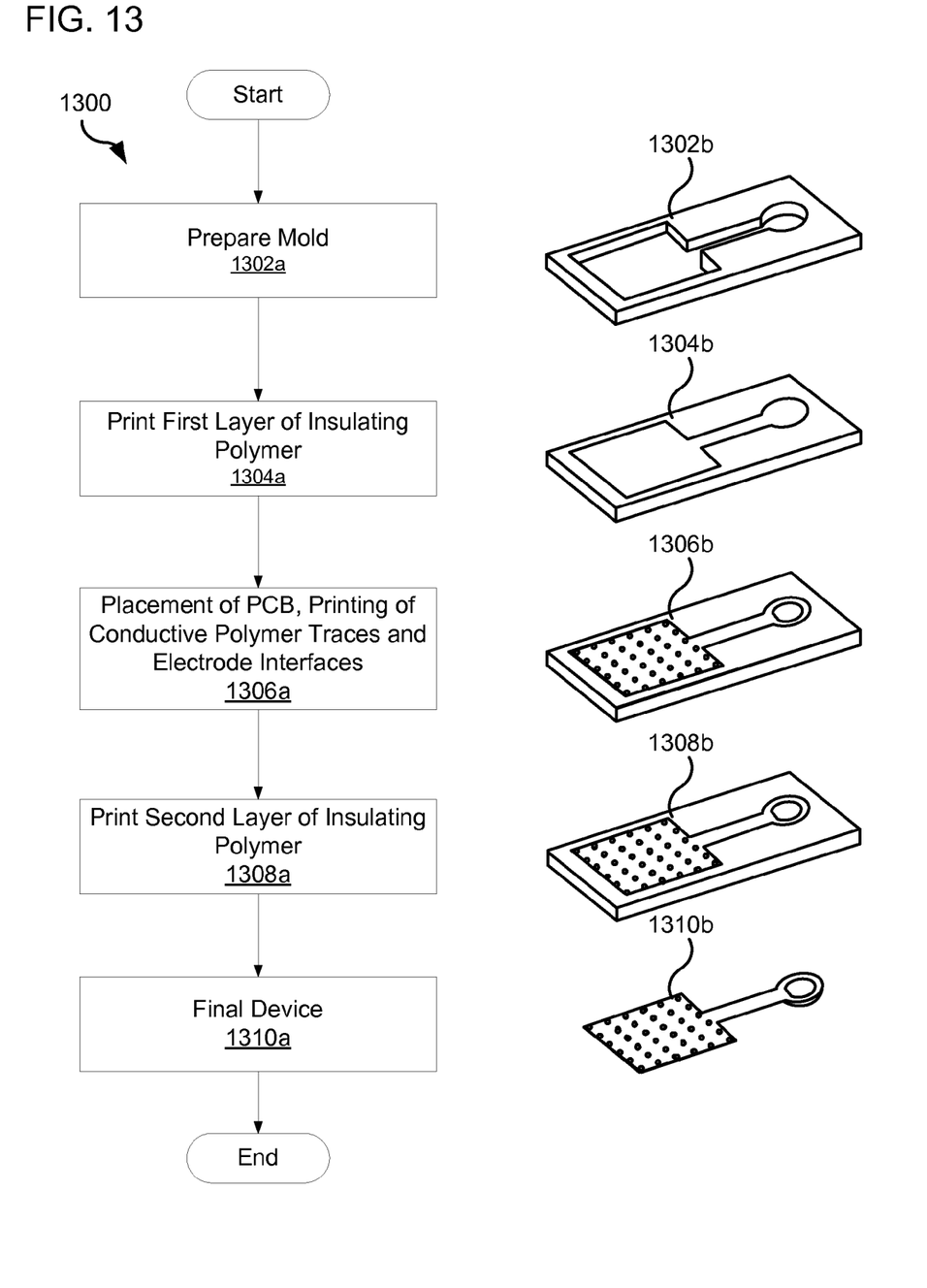
FIG. 13 illustrates one embodiment of a method for manufacturing an electrode array and an associated telemetry module.

FIG. 13 illustrates one embodiment of a method 1300 for manufacturing an electrode array and an associated telemetry module. Also shown in FIG. 13 is an illustration of each step of method 1300. In the illustrated embodiment, the electrode array comprises medical grade polymers, with insulating polymer forming the main body and a conductive, particle-filled polymer of similar formulation providing the conductive traces and active electrode sites. According to various embodiments, the electrode array may be formed with blunt and/or soft edges that allow pushing into spaces while minimizing the changes of cutting and/or rupturing vasculature and other sensitive tissues (for example, minimizing chances of cutting blood vessels within subdural and epidural spaces in the head). The electrode array and associated telemetry module may be created in a layer-by-layer buildup of materials, with the conductive traces disposed between insulating layers. Each layer of the device may be deposited in a variety of ways, such as by a programmable XYZ robotic dispensing system.

At 1302, a mold may be prepared. The mold may take on a variety of shapes, as dictated by the particular application for which the device is to be utilized. The mold may be fabricated from a variety of materials, such as fluoropolymers. Alternatively, a flat plate may be used instead of a mold. The base layer of insulating polymer may be dispensed in the desired pattern and each subsequent layer following a similar pattern. Surface tension of the dispensed material may be sufficient to produce a fabricated device in a desired shape. Further, the shape of an electrode array may be adjusted at the time of implantation. For example, a surgeon may trim the electrode array in order to suit a particular application.

A base layer of insulating polymer (e.g., silicone) may be dispensed into the prepared mold, at 1304. A printed circuit board (PCB) with electronic components may be pressed into a well in the mold using an alignment fixture, level with the surrounding substrate layer at 1306. Further, at 1306, conductive polymer traces and electrode interfaces may be printed. At 1308, a second layer of insulating polymer may be printed. The second layer of insulating polymer may be applied over the signal traces and around the electrode interfaces. Partial curing and plasma surface treatments may be used between deposition steps to enhance bonding.

The following criteria may be utilized in evaluating suitable materials for use in connection with method 1300: pre-cure viscosity; surface tension for dispensing without the aid of a mold; curing properties; post-cure rigidity; adhesion between layers; ability to act as a carrier for the conductive particles.

Commercially available medical grade conductive silicones may be utilized in connection with 1300, and are available from NuSil in Carpinteria, Calif., and Creative Materials in Tyngsboro, Mass.

It will be obvious to those having skill in the art that many changes may be made to the details of the above-described embodiments without departing from the underlying principles of the invention. The scope of the present invention should, therefore, be determined only by the following claims.

The invention claimed is:

1. An apparatus, comprising:
an electrode interface;
a conductive trace in electrical communication with the electrode interface;
an insulating layer disposed around the conductive trace and disposed around at least a portion of the electrode interface;
wherein the electrode interface, the conductive trace, and the insulating layer each comprise one or more polymers, and the conductive trace further comprises a plurality of distinct conductive particles, at least a plurality of the distinct conductive particles being separated by the one or more polymers.

2. The apparatus of claim 1, wherein the plurality of distinct conductive particles comprises at least one of: conductive forms of carbon, metal particles, and composite materials comprising an interior particle coated with metal.

3. The apparatus of claim 1, wherein the conductive trace comprises a plurality of distinct conductive micro-particles.

4. The apparatus of claim 1, wherein each of the electrode interface, the conductive trace, and the insulating layer are homogenous.

5. The apparatus of claim 1, wherein each of the electrode interface, the conductive trace, and the insulating layer are heterogeneous.

6. The apparatus of claim 1, wherein the conductive trace and the insulating layer comprise one or more polymers that shrink and cause compression of the plurality of distinct conductive particles.

7. The apparatus of claim 1, wherein the conductive trace comprises a conductive polymer.

8. The apparatus of claim 7, wherein the conductive polymer comprises one of polypyrrole, polyacetylene, polyaniline, and polydioctyl-bithiophene.

9. The apparatus of claim 1, wherein the insulating layer is transparent to an optical or infrared signal.

10. The apparatus of claim 1, further comprising:
a plurality of electrical components in electrical communication with the conductive trace.

11. The apparatus of claim 10, further comprising:
a printed circuit board to interconnect the plurality of electrical components and the conductive trace; and
wherein the insulating layer is disposed around the circuit board.

12. The apparatus of claim 1, wherein the electrode interface and the insulating layer each comprise a material safe for prolonged contact with internal tissues of a living organism.

13. The apparatus of claim 1, wherein the electrode interface comprises a material safe for prolonged contact with neural tissue.

14. The apparatus of claim 1, further comprising:
a plurality of electrode interfaces;
a plurality of conductive traces, each of the plurality of conductive traces in electrical communication with at least one of the plurality of electrode interfaces.

15. The apparatus of claim 14, further comprising:
a plurality of signal processing components in electrical communication with the plurality of electrodes through a plurality of external interfaces that are fewer in number than the plurality of electrodes; and
a percutaneous connector in electrical communication with the plurality of external interfaces.

16. The apparatus of claim 14, wherein the insulating layer comprises a plurality of layers, each layer being at least partially insulated against adjacent layers, and wherein the plurality of conductive traces are disposed within the plurality of insulating layers.

17. The apparatus of claim 1, further comprising:
a plurality of electrode interfaces; and
a plurality of conductive traces, each of the plurality of conductive traces in electrical communication with at least one of the plurality of electrode interfaces.

18. The apparatus of claim 1, further comprising:
a connector assembly interface in electrical communication with the conductive trace.

19. The apparatus of claim 18, further comprising:
a percutaneous connector assembly.

20. The apparatus of claim 1, wherein the one or more polymers comprise an elastomeric polymer.

21. The apparatus of 20, wherein the elastomeric polymer is stretchable by at least 25%.

22. The apparatus of 20, wherein the elastomeric polymer is stretchable by at least 10%.

23. The apparatus of claim 1, further comprising:
a stimulator in electrical communication with the conductive trace to generate an electrical signal to be transmitted to the electrode interface.

24. The apparatus of claim 1, further comprising:
an amplifier in electrical communication with the conductive trace and configured to receive a signal transmitted by the conductive trace and amplify the signal.

25. The apparatus of claim 1, wherein the insulating layer is continuous along the entirety of the conductive trace.

26. The apparatus of claim 1, wherein the conductive trace has an electrical impedance between 0.01 and 1,000 ohms per centimeter.

27. A system, comprising:
an electrode assembly, comprising:
a plurality of electrodes;
a plurality of electrode interfaces, each of the plurality of electrode interfaces associated with one of the plurality of electrodes;
a plurality of conductive traces, each of the plurality of conductive traces further comprising a plurality of distinct conductive particles, at least a plurality of the distinct conductive particles being disposed within and suspended by the one or more polymers, each of the plurality of conductive traces in electrical communication with at least one of the plurality of electrode interfaces;
a telemetry module in electrical communication with the electrode assembly, the telemetry module comprising:
a telemetry module data communications system;
a telemetry module power system;
an insulating layer disposed around the plurality of conductive traces, disposed around at least a portion of each of the plurality of electrode interfaces, and disposed around the telemetry module;
wherein the plurality of electrode interfaces, the plurality of conductive traces, and the insulating layer each comprise one or more polymers, and the plurality of conductive traces further comprise a plurality of distinct conductive particles.

28. The system of claim 27, wherein the plurality of electrodes are disposed in a grid.

29. The system of claim 27, further comprising a plurality of electrical components in electrical communication with the plurality of conductive traces, and wherein the insulating layer is disposed around the plurality of electrical components.

30. The system of claim 29, further comprising:
a printed circuit board to interconnect the plurality of electrical components and the plurality of conductive traces, and wherein the insulating layer is disposed around the printed circuit board.

31. The system of claim 27, wherein the telemetry module power system further comprises a coil to receive power by way of inductive coupling in electrical communication with the electrode assembly.

32. The system of claim 27, wherein the telemetry module power system further comprises a battery.

33. The system of claim 27, wherein the telemetry module data communications system further comprises a first wireless data transceiver.

34. The system of claim 33, wherein the first wireless data transceiver comprises an infrared transceiver.

35. The system of claim 33, wherein the first wireless data transceiver comprises a radio frequency transceiver.

36. The system of claim 33, wherein the first wireless transmitter comprises an infrared transmitter.

37. The system of claim 33, further comprising a receiver module.

38. The system of claim 37, wherein the receiver module further comprises a second wireless transceiver to communicate data with the first wireless transceiver.

39. The system of claim 38, wherein the receiver module further comprises an alignment indicator configured to provide an indication of the alignment of the receiver module with respect to the first wireless transmitter based on the strength of a data signal transmitted between the first wireless transmitter and the second wireless transmitter.

40. The system of claim 39, wherein the alignment indicator comprises a light emitting diode.

41. The system of claim 38, further comprising an interface adapter configured to couple to a neural instrumentation system.

42. An apparatus, comprising:
an electrode interface;
a conductive trace formed by a first polymer doped with a plurality of distinct conductive particles, at least a plurality of the plurality of distinct conductive particles being disposed within and suspended by the one or more polymers, the conductive trace in electrical communication with the electrode interface;
an insulating layer disposed around the conductive trace and disposed around at least a portion of the electrode interface.

43. The apparatus of claim 42, wherein the first polymer comprises an insulating polymer.

44. The apparatus of claim 43, wherein the insulating polymer is selected from the group consisting of: silicones, siloxanes, polydimethylsiloxane (PDMS), rubber materials, latex materials, polyesters, polypropylenes, polytetrafluoroethylenes (PTFE), Parylenes, liquid crystal polymers, polyimides, polyesterimides, polyamides, polybutyldienes (PBD), polyurethanes, and flexible copolymers.

45. The apparatus of claim 42, wherein the electrode interface and the insulating layer each comprise the first polymers.

46. The apparatus of claim 42, wherein the electrode interface and the insulating layer each comprise a second polymer.

47. The apparatus of claim 46, wherein the second polymer exhibits a compressive force upon the plurality of distinct conductive particles.

* * * * *